United States Patent
Huffa et al.

(10) Patent No.: US 11,766,347 B2
(45) Date of Patent: *Sep. 26, 2023

(54) FUNCTIONAL KNIT ORTHOPEDIC DEVICE

(71) Applicant: OSSUR HF, Reykjavik (IS)

(72) Inventors: Concetta Maria Huffa, Foothill Ranch, CA (US); Harry Duane Romo, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 362 days.

This patent is subject to a terminal disclaimer.

(21) Appl. No.: 16/913,137

(22) Filed: Jun. 26, 2020

(65) Prior Publication Data

US 2020/0323674 A1 Oct. 15, 2020

Related U.S. Application Data

(63) Continuation of application No. 15/680,610, filed on Aug. 18, 2017, now Pat. No. 10,716,694, which is a
(Continued)

(51) Int. Cl.
*A61F 5/01* (2006.01)

(52) U.S. Cl.
CPC .......... *A61F 5/0102* (2013.01); *A61F 5/0106* (2013.01); *A61F 5/0109* (2013.01);
(Continued)

(58) Field of Classification Search
CPC .... A61F 5/0102; A61F 5/0106; A61F 5/0109; A61F 5/0123; A61F 2005/0172; A61F 2005/0176

See application file for complete search history.

(56) References Cited

U.S. PATENT DOCUMENTS 3,786,804 A * 1/1974 Lewis .................. A61F 5/0125
2/24
4,176,665 A 12/1979 Terpening
(Continued)

FOREIGN PATENT DOCUMENTS

| EP | 2283795 A1 | 2/2011 |
| FR | 2807644 A1 | 10/2001 |
| WO | 2012/003992 A1 | 1/2012 |

OTHER PUBLICATIONS

Brochure, "BORT Asymmetric Plus, Die Mehrwert-Orthese bei Patella-Luxation", downloaded Aug. 2012. 16 pages. Retrieved at http://www.bort.com.
(Continued)

*Primary Examiner* — Keri J Nelson
(74) *Attorney, Agent, or Firm* — WORKMAN NYDEGGER (57) ABSTRACT

An orthopedic device includes a textile panel having interior and exterior surfaces, and a first stabilizer assembly including a first tubular welt sewn or knitted within and extending from an exterior surface of the textile panel. A first cable is slidably extending through the tubular welt and a strap is connected to a first end of the cable extending from a first opening of the welt, and the strap is adjustably securable over the textile panel. The orthopedic device may include various portions of stretchability and features for receiving components for the orthopedic device.

4 Claims, 5 Drawing Sheets

Related U.S. Application Data continuation of application No. 14/247,613, filed on Apr. 8, 2014, now Pat. No. 9,744,063.

(60) Provisional application No. 61/809,550, filed on Apr. 8, 2013.

(52) U.S. Cl.
CPC .... *A61F 5/0123* (2013.01); *A61F 2005/0172* (2013.01); *A61F 2005/0176* (2013.01)

(56) References Cited

U.S. PATENT DOCUMENTS

| | | | |
|---|---|---|---|
| 4,201,203 A | 5/1980 | Applegate |
| 4,379,463 A | 4/1983 | Meier et al. |
| 4,870,956 A | 10/1989 | Fatool et al. |
| 4,887,590 A | 12/1989 | Logue et al. |
| 5,036,837 A | 8/1991 | Mitchell et al. |
| 5,139,477 A | 8/1992 | Peters |
| 5,277,697 A | 1/1994 | France et al. |
| 5,334,135 A | 8/1994 | Grim et al. |
| 5,385,538 A | 1/1995 | Mann |
| 5,538,488 A | 7/1996 | Villepigue |
| 5,695,452 A | 12/1997 | Grim et al. |
| 5,728,057 A | 3/1998 | Ouellette et al. |
| 5,730,710 A | 3/1998 | Eichhorn et al. |
| 5,769,809 A | 6/1998 | Witzel |
| 5,823,981 A | 10/1998 | Grim et al. |
| 5,865,776 A | 2/1999 | Springs |
| 6,149,616 A | 11/2000 | Szlema et al. |
| 6,592,539 B1 | 7/2003 | Einarsson et al. |
| 6,634,190 B2 | 10/2003 | Didier-Laurent |
| 6,755,051 B2 * | 6/2004 | Israel ................. A41B 9/00 66/8 |
| 7,083,586 B2 | 8/2006 | Simmons et al. |
| 7,273,464 B2 | 9/2007 | Reinhardt |
| D574,084 S | 7/2008 | Reinhardt |
| 7,473,236 B1 | 1/2009 | Mathewson |
| 7,517,331 B2 | 4/2009 | Reinhardt et al. |
| 7,625,350 B2 | 12/2009 | Hunter et al. |
| 7,749,181 B2 | 7/2010 | Simmons et al. |
| 7,819,830 B2 | 10/2010 | Sindel et al. |
| 7,862,527 B2 | 1/2011 | Gramza et al. |
| 7,959,590 B2 | 6/2011 | Scott |
| 8,025,632 B2 | 9/2011 | Einarsson |
| 8,043,242 B2 | 10/2011 | McSpadden et al. |
| 8,048,014 B2 | 11/2011 | Brown |
| 8,066,654 B2 | 11/2011 | Sandifer et al. |
| 8,118,765 B2 | 2/2012 | Magnusson |
| 8,328,747 B2 | 12/2012 | Matsunaga |
| 9,393,147 B2 | 7/2016 | Scheuermann et al. |
| 10,716,694 B2 * | 7/2020 | Huffa .................... A61F 5/0109 |
| 2005/0020951 A1 | 1/2005 | Gaylord et al. |
| 2007/0060853 A1 | 3/2007 | Sindel et al. |
| 2009/0156973 A1 | 6/2009 | Scott |
| 2010/0036303 A1 | 2/2010 | Bauerfeind et al. |
| 2010/0106070 A1 | 4/2010 | Schlomski et al. |
| 2012/0165714 A1 | 6/2012 | Forbes et al. |
| 2012/0277649 A1 | 11/2012 | Matsuo et al. |
| 2012/0310129 A1 * | 12/2012 | Johnson ............... A61F 5/0118 602/20 |
| 2013/0110023 A1 | 5/2013 | Scheuermann et al. |

OTHER PUBLICATIONS

International Search Report from International Application No. PCT/US2014/033265, dated Jul. 10, 2014.

Product Information, "BORT AsymmetricPlus, No. 114700, Unit PCE", downloaded Mar. 31, 2014, 3 pages. Retrieved at http://shop.bort.de/en/produkt-details.aspx?ProductNo=114700.

Product Information, "BORT AsymmetricPlus, No. 114900, Unit PCE", downloaded Mar. 31, 2014, 3 pages. Retrieved at http://shop.bort.de/en/produkt-details.aspx?ProductNo=114900.

* cited by examiner

FUNCTIONAL KNIT ORTHOPEDIC DEVICE

FIELD OF ART

The embodiments of this disclosure are directed to an orthopedic device, particularly to a functional knit orthopedic device arranged for intimately fitting, and immobilizing, restricting or guiding anatomical segments or joints.

BACKGROUND

Orthopedic braces and supports should restrict, inhibit, immobilize or otherwise control motion about anatomical segments or joints of the human body. Known braces and supports usually incorporate rigid members and hinges located about the region to be immobilized. Historically, orthopedic bracing has tended toward greater rigidity to provide ultimate immobilization with a reduced margin of error in mobility, thus many device designs are over-engineered.

There is an inverse relationship between the rigidity of the device and patient comfort/compliance. The more rigid the device is, the less likely the patient will wear it, especially over extended periods of time. If the patient removes a required device to increase their level of comfort, it ultimately reduces the functional outcome of rehabilitation.

For several pathologies, rigidity in the traditional sense may not be required. For instance, if it is possible to treat a hip pathology through appropriate restriction of hip motion without rigid members and without sacrificing outcomes or patient safety, this could greatly enhance patient comfort and compliance as they work through their rehabilitation protocol. Increased compliance to the treatment regimen leads to optimizing outcomes.

SUMMARY

A functional knit orthopedic device arranged for intimately fitting the limb and joint of the user solves the problem of rigid braces and supports deterring a user from use and not facilitating joint motion activities. The orthopedic device may have restrictive cables and/or restrictive bands or regions integrated into the construction of the device to restrict and guide the joint. These restrictive cables and/or restrictive bands may be formed from metallic yarns, fusible, thermoplastic fibers, elastics, or other suitable materials and elements. They may be knit or inlayed during construction of the fabric brace.

The embodiments of the orthopedic device define a compliant yet comfortable garment, such as a sleeve or other article, arranged to biomechanically provide motion restriction/facilitation of a joint or body segment. The embodiments are preferably adjustable in functional capacity to match the biomechanical requirements of the user's treatment plan throughout rehabilitation. The orthopedic device includes various comfort factors to facilitate maximal compliance of the user over the duration of their treatment such as profile, breathability, compression, flexibility and rigidity.

The human body has a propensity for physiologic learning whereby the individual may, over time, memorize a movement pattern. Professional golfers, gymnasts, and other athletes routinely utilize this capacity through rigorous and repetitive training activities. Over multiple iterations of an activity, they hone their particular skills to a level of perfection in force generation and motion. Over the process they optimize the timing, coordination and amplitude of muscular contraction. After sufficient iterations, the body will literally memorize the biomechanical pattern of force and motion so it can be reproduced on demand.

As the orthopedic device can be key in facilitating desired motions, it offers function beyond simple restriction/facilitation of a range of motion. The embodiments of the orthopedic device may be arranged to guide the user to learn a new set of motor activation patterns/motor control strategies to promote proper activity based biomechanics or even prevent at-risk positioning of the joint(s) or body segment.

Embodiments of the orthopedic device incorporate knitted textiles offering indication-appropriate support, created to a prescribed shape directly on the knitting loom. The creation of required supportive regions include a plurality of textile elements combine into one fabric support panel or functional knit of unitary construction. Embodiments of these textile structures rely in part on yarn selection, including yarns such as performance, moisture management polyesters, strength (Kevlar), steel, cotton, nylons, conductive fibers, yarns, rubber, elastic, silicone and others.

According certain embodiments, a first area is formed of a first stitch configuration, and the second area is formed of a second stitch configuration, different from the first stitch configuration to impart varying structure textures to a surface of the textile element. Many these distinct regions may be combined in series or parallel to generate the appropriate functional knit. Various warp knitting, circular knitting, or weft (flat) knitting processes may form the whole textile element.

Functional knit orthopedic device embodiments may include control of joint range of motion including specific motion inhibition or restriction or prevention. The control is obtained through altering tension in a garment, sleeve or other knit article on a tangent to the skin, thus controlling motion through shear loads (at a tangent to the skin). Control of joint range of motion and soft tissue may be obtained through compression or loading, at or near a direction normal to the surface of the skin and/or garment.

In an embodiment of the disclosure, the orthopedic device is a knee support. The knee support may be formed as a sleeve and comprise first and second stabilizer assembly located above and below the patella area. Each of the first and second stabilizer assemblies may include a plurality of integrally formed tubular welts knitted with a padded area knit into its exterior surface above and below the patella area and laterally extending from the knee area. Each knit welt comprises a free sliding cable anchored at one end near the patella area, and wherein the opposite end of each cable is adapted for attachment to adjustable straps on the calf and thigh in order to provide a way to adjust the patella buttress. The cables are configured to skew freely within a corresponding welt to adjust to the shape of the knee area and angle of the attached straps as attached to both the calf and thigh areas.

According to one embodiment, the cables are knit into the panel, therefore removing the necessity to be applied afterwards. As an alternative, the welts are formed first and then the cables are provided within the welts.

First and second straps may be connected to a first end of the first and second cables, respectively, and extending from a first opening of the first and second welts. The first and second straps adjustably secure over the textile panel and are individually securable relative to one another. A pad having a first portion connects to a second end of the first cable extending from a second opening of the welt, and a second portion of the pad connects to a second end of the second cable extending from a second opening of the welt. The first and second straps are adjustable to urge movement of the pad.

The knee support may be made from an elastic textile material and comprises a plurality of integrated elastic 3-sided pockets on the upper and lower portions of its exterior surface. These pockets correspond to the lateral and medial sides of the sleeve and are configured to hold posts for connecting to and securing a hinge stable. The pocket openings are preferably narrow with bottom portions that are wider to accommodate wide posts, and constricted for preventing the posts from popping out.

The knee support may also comprise an open-ended vertical tubular pocket on its interior surface between the patella and popliteal areas. This pocket is configured to position a silicon J buttress on the brace interior for supporting and stabilizing the patella.

The patella area of the knee support may comprise a loose knit elastic stretch fabric for patella relief and placement, which contrasts in color from the rest of sleeve. The popliteal area may comprise an elastic mesh fabric for venting and to prevent bunching of the material. The popliteal area preferably defines a diamond-like geometric shape for dimensional stability and comfort.

Further, a stiff spacer material having a gradient configuration may be integrated between the patella area and popliteal area to stabilize the knee. The gradient spacer on the medial side of the sleeve descends in a direction toward the patella to disperse stress in the area. The narrow part of the gradient may be positioned adjacent to the patella area, and the wide part of the gradient may be positioned adjacent to the popliteal area.

The knee support may also include a plurality of elastic horizontal ribbing on its posterior side to avoid bunching of material and to assist with compression. Further, a tubular knit binding on the upper and lower edge portions of sleeve may be adapted to not cut into skin to provide additional comfort to a user.

BRIEF DESCRIPTION OF THE DRAWINGS

These and other features, aspects, and advantages of the present invention will become better understood regarding the following description, appended claims, and accompanying drawings.

In the various figures, similar elements are provided with similar reference numbers. The drawing figures are not drawn to scale, or proportion, but instead are drawn to provide a better understanding of the components, and are not intended to be limiting in scope, but rather provide exemplary illustrations.

DETAILED DESCRIPTION OF VARIOUS EMBODIMENTS

A. Fabrication of Various Embodiments

Various embodiments of the orthopedic device may utilize flat knitting, which allows production of textile structures into a final desired shape so there is no cutting and very minimal waste. Flat knitted elements are formed directly in the desired three-dimensional shapes or modular panels, which can help avoid the need to use additional support structures.

In engineering the stitches to stretch, restrict, pad or contour to body shapes, using multiple types of yarns and/or combined stitch patterns at strategic placements, several desired performance characteristics can be localized into performance zones within a single, unitary construction. Various pockets, channels and tunnels can be formed by the knitting to introduce: restrictive stays, pads, hot/cold packs, hyper elastic materials, inflatable pouches (liquid or air), webbing, hardware, and other customizable elements of bracing and support. Inflatable areas in the knit pouches can exert pressure and force on the desired areas and are customized to patient's condition.

Embodiments of the functional knit orthopedic device preferably form a knitted textile bracing-support having a shape created on the knitting loom including, but not limited to, various warp knitting, circular knitting, or weft (flat) knitting processes.

Embodiments of the functional knit orthopedic device may take the form of a garment. Support areas may include several textile elements combined into one textile support panel with unitary construction or a group of modular panels required for treating a medical indication. The body of the textile panel or panel grouping provides for biomechanical range of motion, compression, and therapeutic elements integrated into a single panel, or panels that may form a garment. Three-dimensional flat knitting allows production of these textile structures into a final desired shape to avoid cutting and waste.

Each panel or series of panels may have areas of gradient levels of stretch, flexure, rigidity, and restrictive elements integrated into the fabric by mapping the appropriate levels of motion or restriction required for a medical indication. This is achieved through a corresponding system of knit stitching techniques that start with yarns. Knit stitching techniques create varying degrees of elasticity, rigidity, open channels, tunnels, intarsia zones of specialized yarns integrated into the base fabric. The first area of knitting is formed of a first stitch configuration, and the second area is formed of a second stitch configuration different from the first stitch configuration to impart varying textures to a surface of the textile element.

The knitted base of the device can comprise natural and/or synthetic yarns: silk, wool, polyester, nylon, olefin, and interlaced with specialty yarns: moisture management, elasticized, fusible, metallic, Kevlar, silicon, and other types of performance yarns knit into fully fashioned, textured, intarsia, or three-dimensional regions and appendages such as connected tubes, circles, open cuboids, straps, spheres and other integrated knit shapes.

Fully-fashioned flat knitted elements may be formed directly in the desired three-dimensional shapes or modular panels, which can help avoid the need to use additional support structures and emerge from the machine ready to be sewn together. This fully fashioned knitting technique adds or drops stitches to create custom two and three-dimensional shapes appropriate to the desired finished garment structure.

The intarsia areas may comprise threads or yarns, which are isolated into specialized zones, using silicon, Kevlar, fusible, nylon monofilament, Dynema, spandex or other specialty performance yarns knit into the fabric to enable that region to perform a specific function. These areas can be arranged into any flat, textured or three-dimensional shape required for load mapping the garment for the specific medical indication.

The load mapped zones may be further achieved by combining knit structures (knit, tuck, miss), transferring loops, dropping or adding needles, segmenting takedown in varying rates across the width of the garment fabric, varying structural elements, inlaying yarns, weft insertion, direct feed, warp insertion, and varying speed of yarns fed into the system.

Besides standard knitting feeders, several types of specialized knitting feeders may isolate, apply and integrate these yarns into the base fabric of this garment: intarsia feeders, in-lay, direct feeders, and plaiting feeders. With the plaiting, the yarn would lay in the isolated area but only on the face or the back of the fabric.

B. Biomechanics of Various Embodiments

Control of joint range of motion includes specific motion inhibition or restriction or prevention. This may be obtained through altering tension in a garment on a tangent to the skin controlling motion through shear loads (at a tangent to the skin). Control of joint range of motion and soft tissue may be assisted through compression or loading, at or near a normal direction to the surface of the skin and/or garment.

In embodiments of the orthopedic device, normal motion may be disrupted through an intimately fitting garment with restrictive bands integrated into constructing the functional knit orthopedic device. The restriction may be created through altering both the yarn and the weave of the fabric. The interface between fabric and skin can vary as well. Some areas would be low stretch and have high friction or tackiness bonding the fabric to the skin. These regions form an anchor for stabilization of the garment to the core and the extremity.

Other textile areas can have high stretch and offer low friction allowing the body segment to move freely. By carefully selecting the anchor zones and orienting restrictive bands within the textile, embodiments can provide restriction or guidance to the joint in question, preventing injurious movement and even encouraging safe motion strategies about the joint.

C. Detailed Description of Knee Support

In observing the orthopedic device of FIGS. 1-4, a knee support 10 includes a textile panel 12 having interior and exterior surfaces and a patella stabilizing assembly 14 incorporated into the textile panel 12. A popliteal relief area 18 is on a posterior side of the support, and at the same height as the patella relief area 16.

The support 10 includes a hinge 20 on each of the lateral and medial sides with upper and lower struts 22, 24 connecting to the hinge. The support 10 may include upper and lower pockets 26, 28 formed by the textile panel 12 into which the upper and lower struts 22, 24 are received and secured. The support may include upper and lower circumferential straps 30, 32 arranged for tightening about the upper and lower leg segments UL, LL of the user. Upper and lower bindings 44, 46 may be at the upper and lower ends of the support 10, and a frictional coating or other frictional feature (not shown) may be in combination with the upper and lower bindings 44, 46 to maintain the support on the upper and lower legs UL, LL.

The patella stabilizing assembly 14 includes upper and lower stabilizer assemblies 34, 36, located above and below, respectively, a patella relief area 16 formed by the textile panel 12 on an anterior side of the support. The upper and lower stabilizer assemblies 34, 36 are connected to a stabilizer pad 38 intended to exert pressure on at least a side of the user's patella P about the user's knee K.

Figure 1:
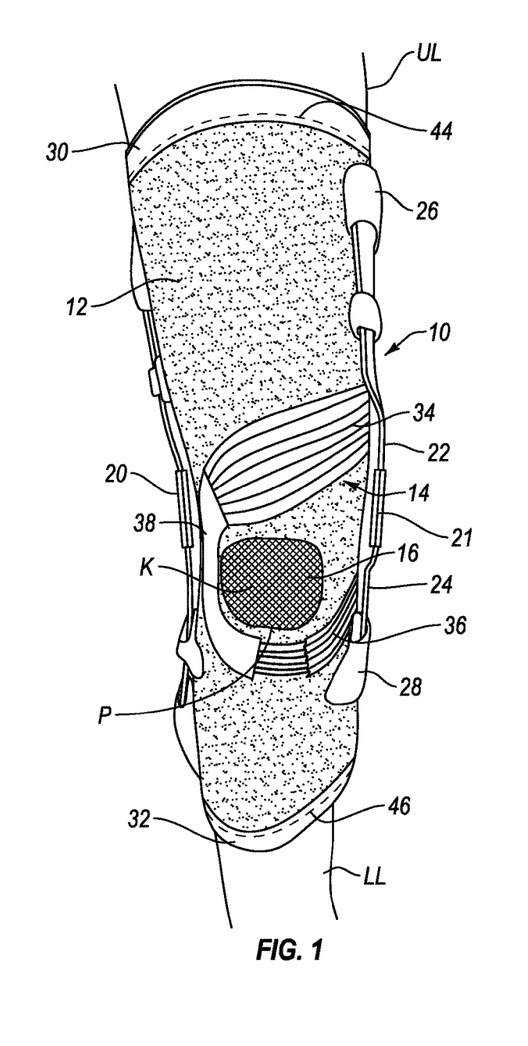
FIG. 1 is a front view of a knee support embodiment of an orthopedic device having an integrated knit textile.
Figure 2:
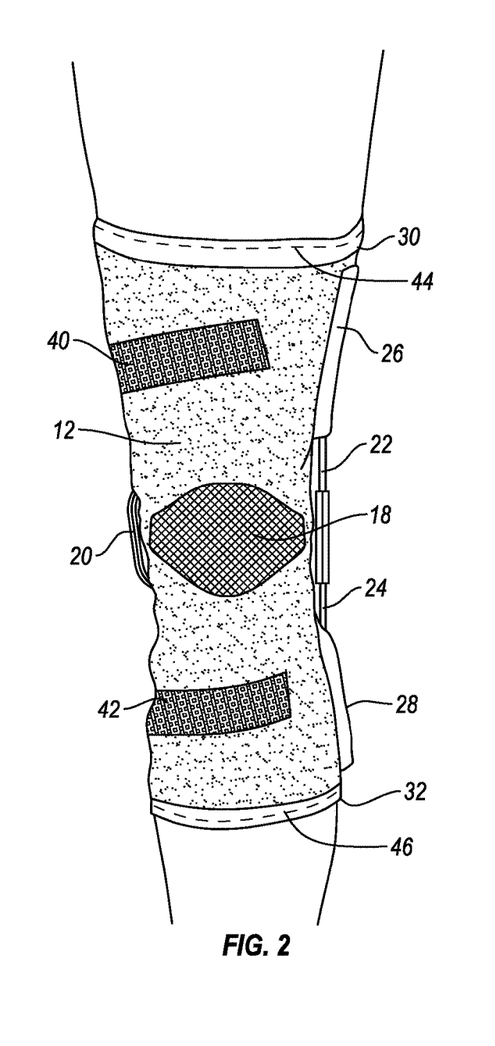
FIG. 2 is a rear view of the knee support of FIG. 1.
Figure 3:
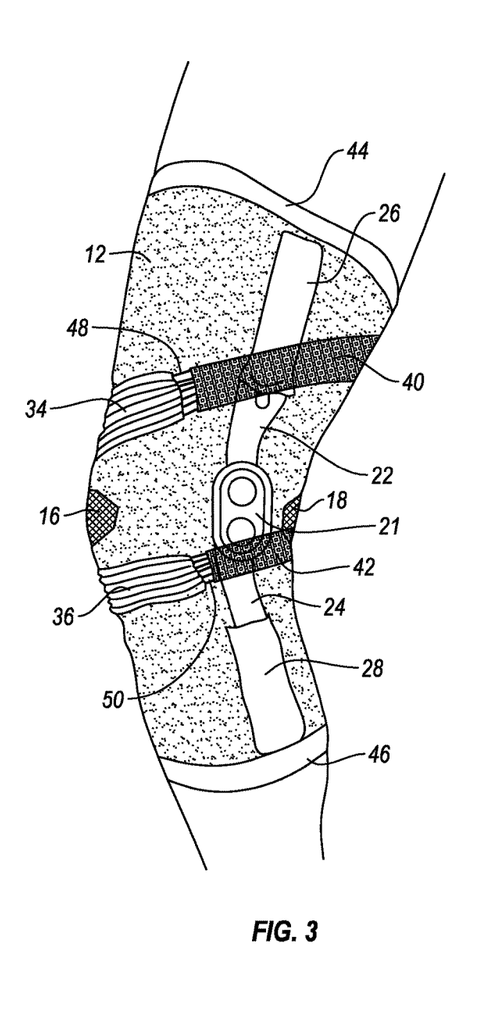
FIG. 3 is a lateral side view of the knee support of FIG. 1.
Figure 4:
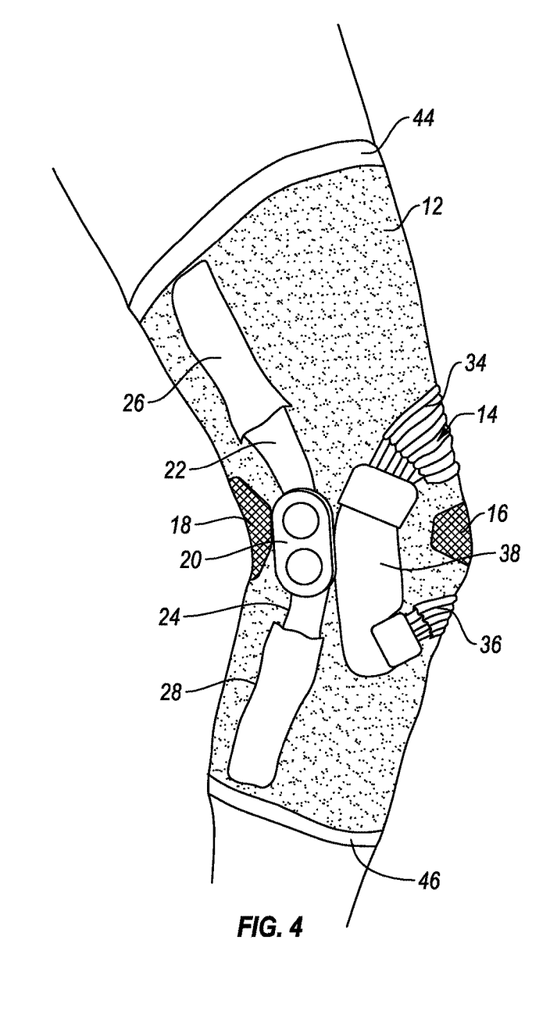
FIG. 4 is a medial side view of the knee support of FIG. 1.

Upper and lower stabilizer straps 40, 42 secure to the upper and lower stabilizer assemblies 34, 36 via upper and lower sets of cables 48, 50, as shown in FIG. 3, retained within the upper and lower stabilizer assemblies 34, 36.

Figure 5:
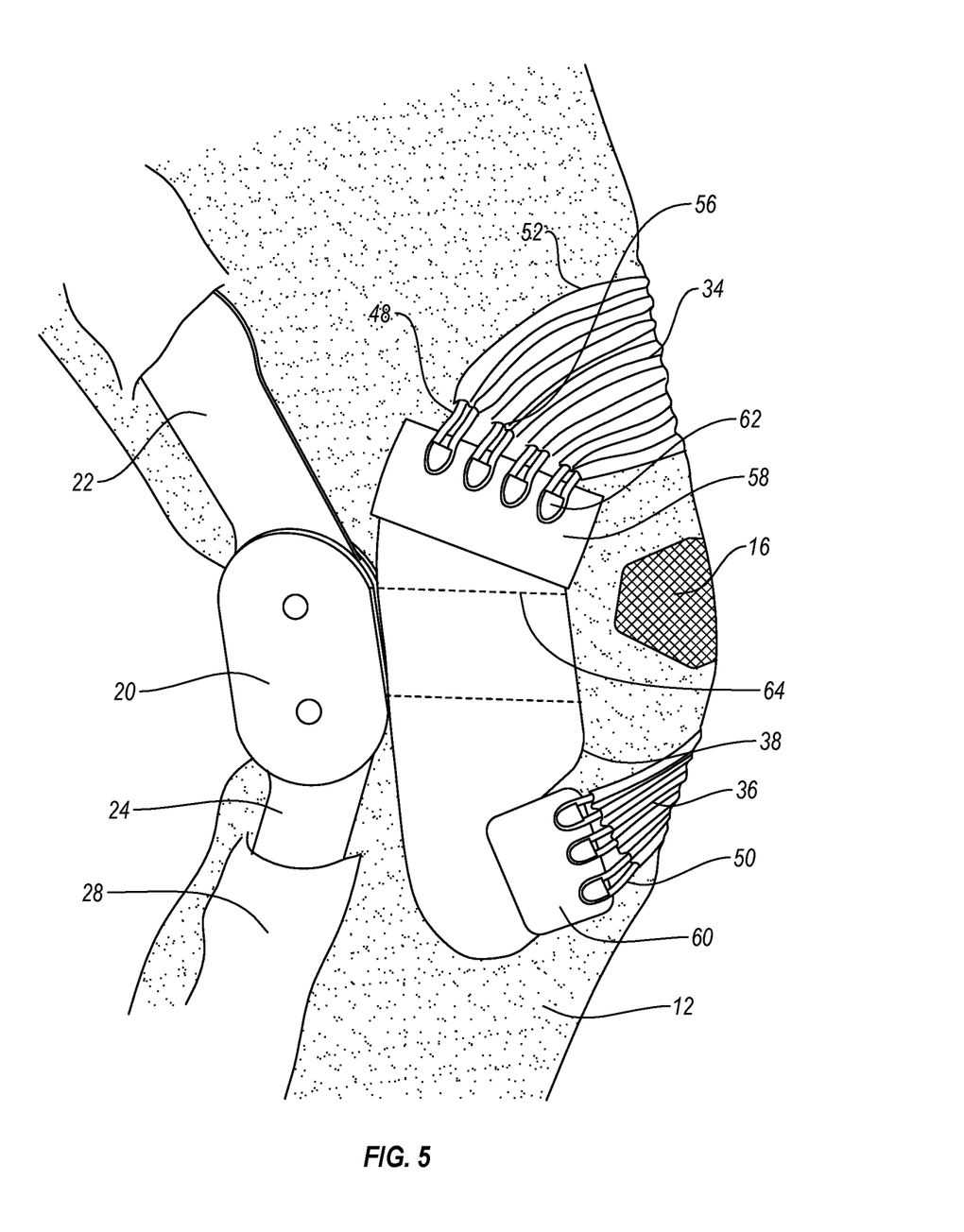
FIG. 5 is a detailed view of the medial side view of FIG. 4.

Turning to FIG. 5, each of the upper and lower stabilizer assemblies 34, 36 includes a series of welts 52, 54, with welt openings 56 defined on opposed sides of the welts 52, 54. The cable sets 48, 50 secure to cable retainers 62 formed by upper and lower brackets 58, 60 carried by the stabilizer pad 38.

The stabilizer pad 38 may be on either of the interior or exterior sides of the textile panel 12. A channel 64 may be on either of the inner or exterior sides of the textile panel 12, and retain the stabilizer pad 38 generally in place or a consistently proximate location relative to the user's patella. The channel 64 may have some stretchability to allow for shifting of the knee as a user walks, or may be non-stretchable.

The upper and lower stabilizer assemblies 34, 36 preferably define the welts 52, 54 as areas for free flowing cables 48, 50 located and suspended within the welts. The welts may include padding and also may be formed over an existing surface of the textile panel to provide padding and assure that any tension applied by the cables is evenly disbursed. The cables themselves are preferably knitted within the welts to minimize assembly and to yet further integrate features of the device.

The ends of the cables are adapted to slide from the welt openings 56 on lateral and medial sides of the knee support 10. The ends of the cables are attached to the upper and lower straps 40, 42 on one side of the brace, as shown in FIG. 3. The straps 40, 42 are adjustably secured over the upper and lower leg segments of the user over portions of the textile panel 12. The ends of the cables on the other side secure to the brackets and are used to adjust pressure exerted on the patella or knee when the straps 40, 42 are tensioned.

The cables 48, 50 freely extend through the tubular welts, and are neither trapped by the fabric forming the welts nor by the stabilizer pad. The cables are also sized more narrowly than the welts, which allow them to skew freely within the welts and therefore adapt to the anatomy of the user's knee and leg. The welts may be oriented at an angle to a direction by which the straps 40, 42 extend to assure the stabilizer pad is in a desirable orientation regardless of the user's anatomy.

According to the embodiment, a single cable 48, 50 flows through and corresponds to each of the stabilizer assemblies 34, 36. The free-flowing cable flows independently within the corresponding set of welts for each of the stabilizer assemblies. Multiple segments of each cable secure to the stabilizer pad, as shown in FIG. 5.

The stabilizer pad may be formed from a polymer, foam, silicone or other suitable material, and is preferably flexible to accommodate the shape of the user's knee. The stabilizer pad may be of a "J" type shape to follow a generally lateral or medial contour of a patella and extend below a user's patella. The stabilizer pad provides shear forces and positions the user's patella. Although the stabilizer pad has a "J" shape, it can have many known patella buttress shapes such as "C," "U," and "O," to name a few.

While the stabilizer pad is shown as extending along a lateral side of the knee support, the knee support may be arranged so the upper and lower stabilizer straps and the stabilizer pad are on opposite sides of the knee. The upper and lower stabilizer assemblies can likewise be reversed in orientation.

Figure 6:
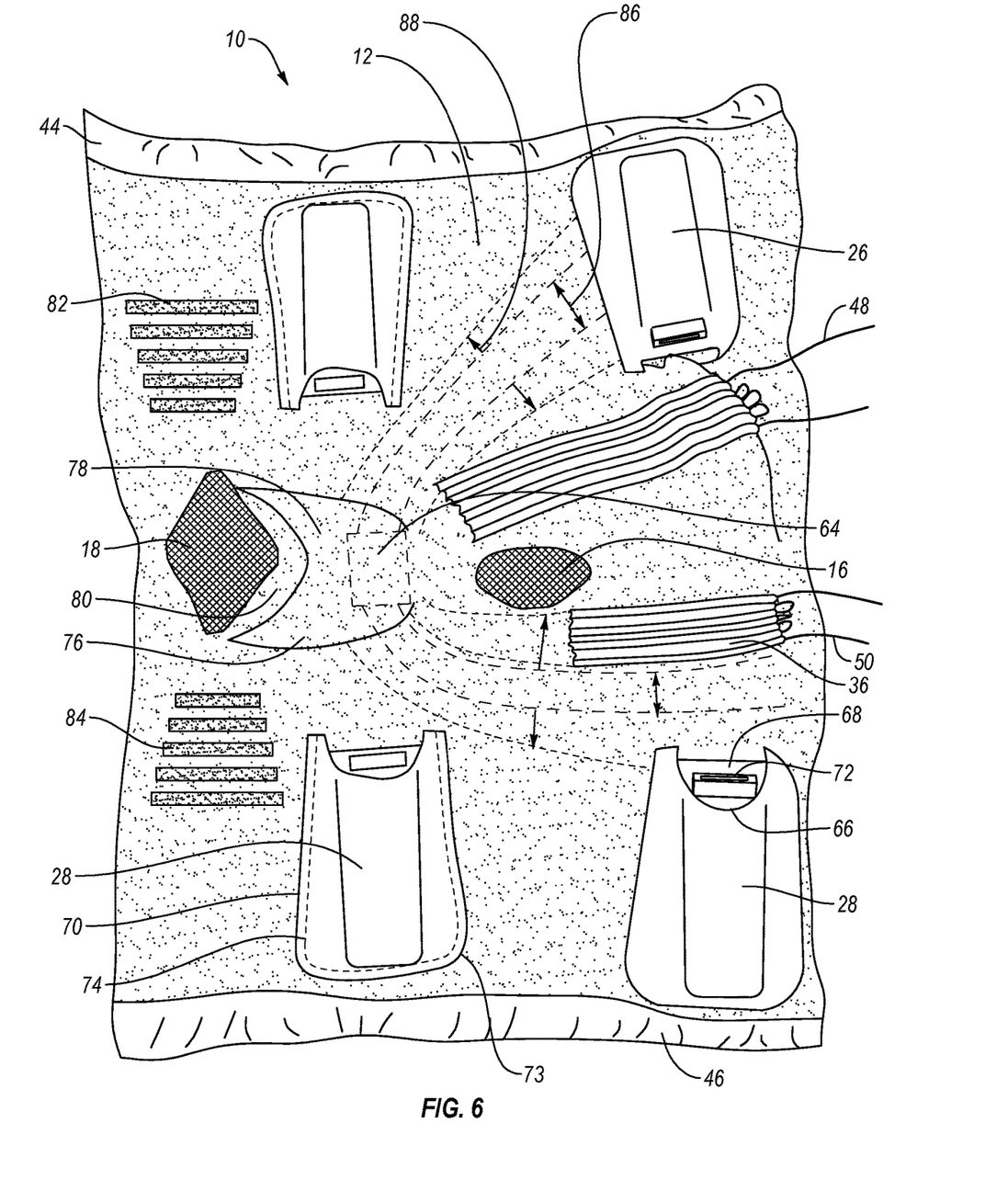
FIG. 6 is a plan view of the integrated knit textile of FIG. 1.

In referring to FIG. 6, the knee support 10 may be made from an elastic textile material and comprise a plurality of integrated elastic 3-sided upper and lower pockets 26, 28 on the upper and lower portions of its exterior surface. These pockets 26, 28 correspond to the lateral and medial sides of the sleeve 10 and are configured to hold stays 68 connecting to and securing to the struts 22, 24 or a hinge 20, as in FIG. 2.

The pockets 26, 28 preferably define narrow openings 66 and have a profile 70, as shown in FIG. 6, with a bottom portion wider to accommodate wide stay shapes. When inserting a stay into a pocket, the opening is expandable to receive the stay and the opening returns to its original shape to constrict the opening for preventing the stay from migrating out from the pocket. Preferably, the stay has a shape, at least at a lower portion, wider than the opening.

As shown in FIG. 6, the stay 68 may define an opening 72 for receiving the struts 22, 24. The profile 74 of the stay may be configured to provide additional support to the struts 22, 24 and distribute pressure over the user's leg at the end of the struts 22, 24 that serve as anchor points for the hinge.

The patella area 16 of the knee support may comprise a loose knit elastic stretch fabric for patella relief and placement, and is provided with a color contrast from the rest of the sleeve. The different color of the patella area 16 informs the user where to properly align the knee support over the knee. The popliteal area 18 may have an elastic mesh fabric for venting and preventing bunching of the material. The popliteal area preferably defines a diamond-like geometric shape for dimensional stability and comfort.

A stiff region 76 may be integrated between the patella area and popliteal area to stabilize the knee, particularly on a side of the knee including the stabilizer pad. The textile panel surrounding or adjacent to the stiff region 76 is preferably more elastic and stretchable than the stiff region 76. The stiff region 76 may define a shape having a gradient configuration 78 in that the gradient configuration 78 descends in a direction toward the patella to distribute stress. The narrow part of the gradient may be positioned adjacent to the patella P (FIG. 8), and the wide portion of the profile of the gradient may be positioned adjacent to or toward the popliteal area.

The gradient configuration 78 is preferably defined along its length, such as the direction between the patella are and the popliteal relief area. The gradient may diminish from the popliteal area toward the patella area.

The stiff region 76 may be formed from a material segment stitched to the textile panel. The material segment may be formed from a spacer material or a plurality of different layers. The gradient configuration can be formed by the shape of the gradient configuration, the knit of the material forming the stiff region, or by a plurality of different layers forming the stiff region with some portions of the stiff region with more layers than others.

A flexible bordering region 80 may be located about the popliteal relief area 18 so as not to impede the flexibility of the user's popliteal. The gradient configuration 78 is oriented to pull toward the outer points of the mesh shape of the popliteal area to avoid bunching of material.

The stiff region 76 and its gradient configuration provide stabilization of the knee in a focused and precise manner. The gradient configuration 78 is arranged to load map the stress exerted on the knee, and more evenly distribute and disperse any stresses exerted in part by the stabilizer pad or from compression of the sleeve over the knee.

The knee support may also include upper and lower stiffener regions 82, 84 including a plurality of elastic horizontal ribbing on its posterior side to avoid bunching of material and to assist with compression. The stiffener regions 82, 84 may include a profile accommodating the anatomy of the user. The upper stiffener region 82 may have tapering horizontal elasticized stitched rows, which follow the taper of the thigh. The lower stiffener region 84 may have horizontal elasticized stitched rows increasing gradually in length as the rows approach the lower end of the sleeve 10.

Figure 7:
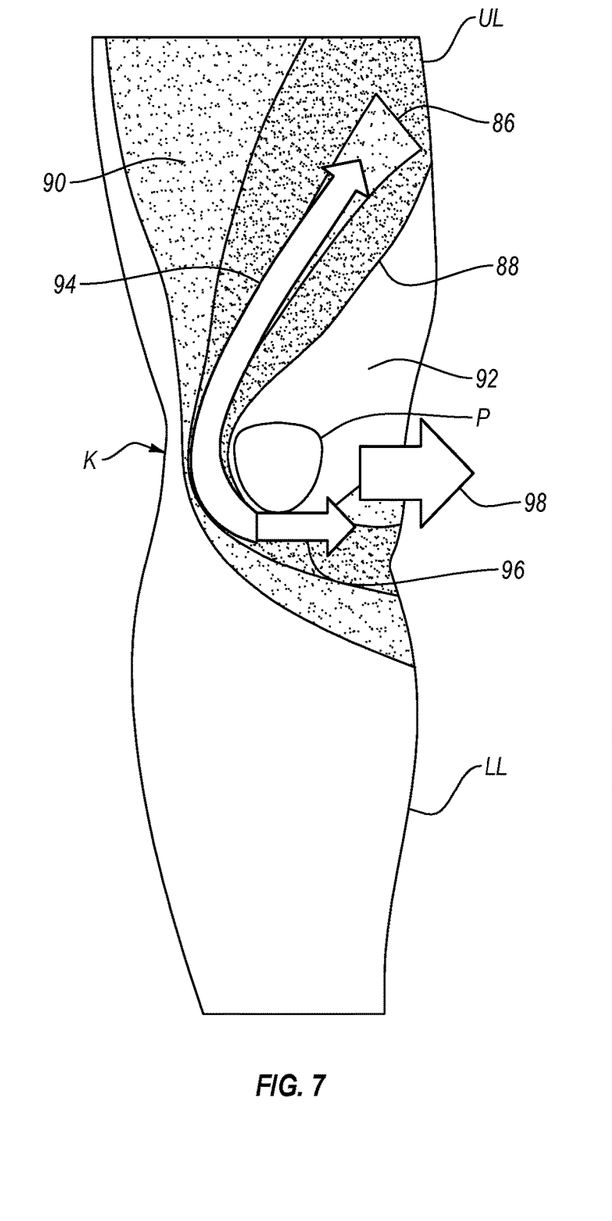
FIG. 7 is a schematic view showing forces on the leg and knee of a user.
Figure 8:
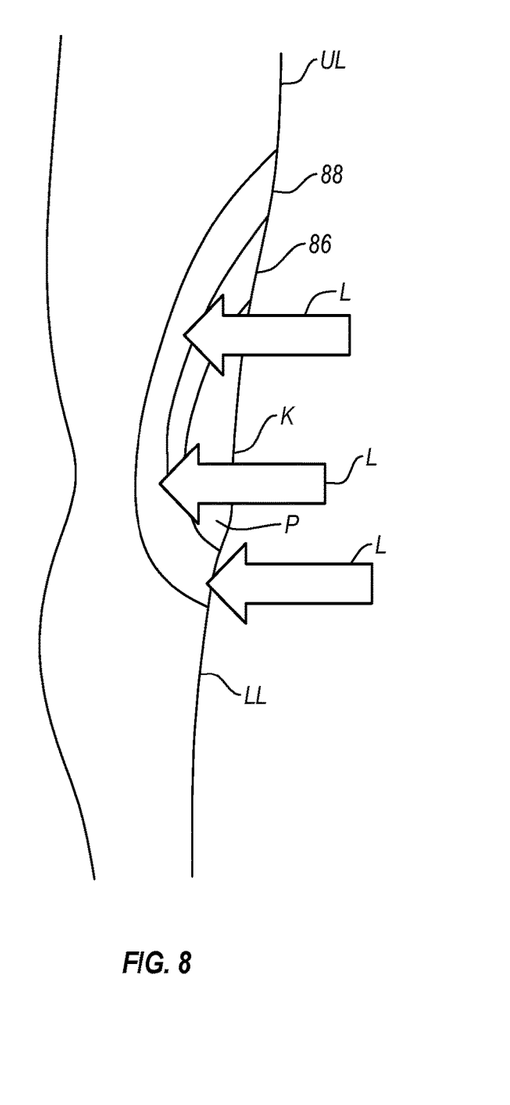
FIG. 8 is another schematic view showing forces on the leg and knee of a user.

In referring to FIGS. 6-8, the sleeve 10 may include a plurality of restrictive bands or regions having different degrees of stretchability. A first band or region 86 has no stretchability, a second band or region 88 has intermediate stretchability, and a third band or region 90 is more stretchable than the second band 88. The bands may be bordered by or located within other bands.

Through the combination of the restrictive bands connected to a zone of non-stretch rigid textile 86, the sleeve can impart a load onto the skin at a normal to the textile. With appropriate orientation, the skin of the user is loaded and it applies a load on the underlying bone and soft tissue of the knee and leg.

It is possible to load around the patella with loaded areas adjoining unrestricted areas (i.e., stretchable bands), and control the position of the patella regarding the Patellofemoral Joint. A reorientation of the patella in this way can affect the way the patella tracks in its femoral groove reducing pain secondary to osteoarthritic degeneration of the anterior compartment of the knee.

According to this embodiment, particularly exemplified in FIG. 7, a non-stretch region is knitted into the sleeve and at the patellar ligament, continuing along lateral border of the patella and extending up the upper leg. Graded rigid to stretch regions 86, 88 extend outward on both sides of the rigid region 84 with generally stretchable material 90, 92 forming some textile panel surrounding these regions. The fit is snug against the skin at rest. As the leg flexes and/or the user's quadriceps fire, tension is created along the non-stretch region as the soft tissue attempts to press upward through the textile.

As shown in FIG. 8, the activity of a leg with the sleeve of FIG. 7 creates a load (at a normal to the garment/skin) along the non-stretch lateral border of the patella and the patellar ligament. Since little or no restriction of motion is provided along the proximal or medial borders 94, 96 of the patella P, the resulting load 98 displaces the patella medially (or laterally depending on its location). A buttress within the sleeve, such as the aforementioned stabilizer pad, along the patellar ligament and lateral border increases the focused load in these areas. Dynamic loading by loads L of the region surrounding region of the lateral buttress and the patella's position are altered medially.

E. Alternatives

While the disclosure discusses specific embodiments for the knee, functional knit orthopedic device embodiments of the disclosure may be used with other limbs, joints and anatomical portions including the torso, shoulder, elbow, wrist/hand, hip, knee, and foot/ankle.

Embodiments of the functional knit orthopedic device may be combined with hot/cold therapy, compression and electrical stimulation modalities such as Transcutaneous Electrical Nerve Stimulation (TENS) or Neuro-Muscular Electrical Stimulation (LAMES).

The invention claimed is:

1. An orthopedic device comprising:
   a tubular sleeve having interior and exterior surfaces, and formed from a textile panel;
   a plurality of restrictive bands having different degrees of stretchability formed by the textile panel;
   wherein a first band has no stretchability, a second band has intermediate stretchability, and a third band is more stretchable than the second band;
   wherein the textile panel defines a non-stretch region formed by a rigid textile construction and arranged to impart a load onto skin of a user normal to the tubular sleeve, the non-stretch region being arranged, and having appropriate orientation, to load the skin of the user and to apply a load on underlying bone and soft tissue of a knee and a leg.

2. The orthopedic device of claim 1, wherein graded rigid regions extend outward on both sides of the non-stretch region and are generally stretchable.

3. An orthopedic device comprising:
   a tubular sleeve having interior and exterior surfaces, and formed from a textile panel;
   a plurality of restrictive bands having different degrees of stretchability formed by the textile panel;
   wherein a first band has no stretchability, a second band has intermediate stretchability, and a third band is more stretchable than the second band;
   wherein a non-stretch region is knitted into the textile panel at a region generally corresponding to a patellar ligament of the tubular sleeve when donned by a user, the non-stretch region arranged to continue along a lateral border of a patella and extend up an upper leg when the tubular sleeve is donned by the user.

4. The orthopedic device of claim 3, wherein graded rigid regions extend outward on both sides of the non-stretch region and are generally stretchable.

* * * * *